(12) United States Patent
Okada

(10) Patent No.: US 10,175,589 B2
(45) Date of Patent: Jan. 8, 2019

(54) QUINONE DERIVATIVE AND ELECTROPHOTOGRAPHIC PHOTOSENSITIVE MEMBER

(71) Applicant: KYOCERA Document Solutions Inc., Osaka (JP)

(72) Inventor: Hideki Okada, Osaka (JP)

(73) Assignee: KYOCERA Document Solutions Inc., Osaka (JP)

( * ) Notice: Subject to any disclaimer, the term of this patent is extended or adjusted under 35 U.S.C. 154(b) by 0 days.

(21) Appl. No.: 15/618,243

(22) Filed: Jun. 9, 2017

(65) Prior Publication Data

US 2017/0363978 A1 Dec. 21, 2017

(30) Foreign Application Priority Data

Jun. 15, 2016 (JP) .................. 2016-118965

(51) Int. Cl.
*G03G 5/06* (2006.01)
*C07C 49/683* (2006.01)
*G03G 5/05* (2006.01)

(52) U.S. Cl.
CPC ......... *G03G 5/0609* (2013.01); *C07C 49/683* (2013.01); *G03G 5/0564* (2013.01);
(Continued)

(58) Field of Classification Search
CPC .. G03G 5/0609; G03G 5/0696; C07C 49/683; C07C 2602/10
See application file for complete search history.

(56) References Cited

U.S. PATENT DOCUMENTS 6,485,873 B1 * 11/2002 Ohkura ............... G03G 5/0605
  430/56
6,593,047 B2 * 7/2003 Azuma ............... G03G 5/0564
  430/56
(Continued)

FOREIGN PATENT DOCUMENTS

JP  2000226354 A  *  8/2000
JP  2005-173292 A    6/2005
JP  2007316099 A  * 12/2007

OTHER PUBLICATIONS

English language machine translation of JP 2007-316099 (Dec. 2007).*

(Continued)

*Primary Examiner* — Christopher D Rodee
(74) *Attorney, Agent, or Firm* — Studebaker & Brackett PC

(57) ABSTRACT

A quinone derivative is represented by general formula (1). In general formula (1), at least one of $R^1$-$R^3$ and at least one of $R^4$-$R^6$ each represent, independently of one another, an alkyl group having 4 to 10 carbon atoms or an alkyl group having 2 to 5 carbon atoms that has an aryl group having 6 to 14 carbon atoms. All other of $R^1$-$R^3$ and all other of $R^4$-$R^6$ each represent, independently of one another, an alkyl group having 1 to 6 carbon atoms, an aryl group having 6 to 14 carbon atoms, or a cycloalkyl group having 3 to 10 carbon atoms.

(Continued)

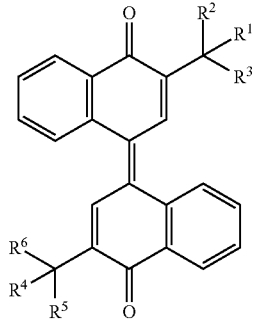

(52) U.S. Cl.
CPC ......... *G03G 5/0607* (2013.01); *G03G 5/0614* (2013.01); *G03G 5/0696* (2013.01); *C07C 2601/14* (2017.05); *C07C 2602/10* (2017.05); *C07C 2603/74* (2017.05)

(56) References Cited

U.S. PATENT DOCUMENTS

| | | | | |
|---|---|---|---|---|
| 10,007,199 | B2* | 6/2018 | Shimizu | G03G 5/04 |
| 2002/0102484 | A1* | 8/2002 | Miyamoto | G03G 5/0605 |
| | | | | 430/58.25 |
| 2016/0282732 | A1* | 9/2016 | Shimizu | G03G 5/0614 |
| 2018/0046098 | A1* | 2/2018 | Shimizu | G03G 5/047 |

OTHER PUBLICATIONS

English language machine translation of JP 2000-226354 (Aug. 2000).*

* cited by examiner

5 Claims, 4 Drawing Sheets

QUINONE DERIVATIVE AND ELECTROPHOTOGRAPHIC PHOTOSENSITIVE MEMBER

INCORPORATION BY REFERENCE

The present application claims priority under 35 U.S.C. § 119 to Japanese Patent Application No. 2016-118965, filed Jun. 15, 2016. The amounts of this application are incorporated herein by reference in their entirety.

BACKGROUND

The present disclosure relates to quinone derivatives and electrophotographic photosensitive members.

An electrophotographic photosensitive member is used in an electrographic image forming apparatus. Examples of the electrophotographic photosensitive member include a single-layer electrophotographic photosensitive member and a multi-layer electrophotographic photosensitive member. The electrophotographic photosensitive member includes a photosensitive layer. The single-layer electrophotographic photosensitive member includes a single-layer photosensitive layer having functions of charge generation and charge transport as a photosensitive layer. The multi-layer electrophotographic photosensitive member includes as a photosensitive layer a combination of a charge generating layer having a function of charge generation and a charge transport layer having a function of charge transport.

An electrophotographic photosensitive member has been known that includes a photosensitive layer containing for example a compound represented by the following chemical formula (E-1) or (E-2).

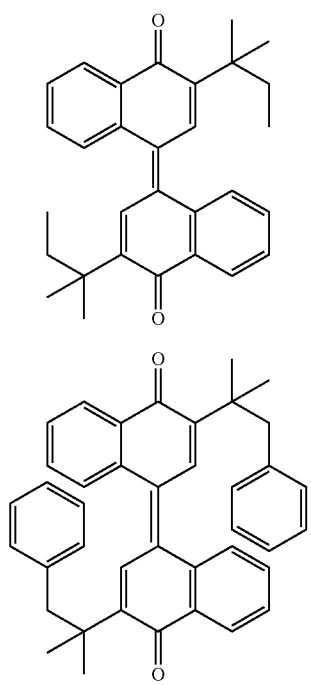

SUMMARY

A quinone derivative according to the present disclosure is represented by general formula (1).

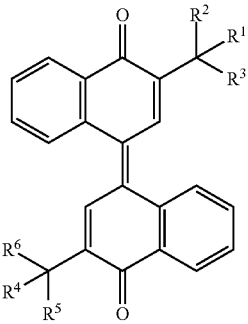

In general formula (1), at least one of $R^1$, $R^2$, and $R^3$ represents an alkyl group having 4 to 10 carbon atoms or an alkyl group having 2 to 5 carbon atoms that has an aryl group having 6 to 14 carbon atoms. All other of $R^1$, $R^2$ and $R^3$ represents an alkyl group having 1 to 6 carbon atoms, an aryl group having 6 to 14 carbon atoms, or a cycloalkyl group having 3 to 10 carbon atoms. At least two of $R^1$, $R^2$, and $R^3$ are optionally bonded together to form a ring. At least one of $R^4$, $R^5$, and $R^6$ represents an alkyl group having 4 to 10 carbon atoms or an alkyl group having 2 to 5 carbon atoms that has an aryl group having 6 to 14 carbon atoms. All other of $R^4$, $R^5$, and $R^6$ represents an alkyl group having 1 to 6 carbon atoms, an aryl group having 6 to 14 carbon atoms, or a cycloalkyl group having 3 to 10 carbon atoms. At least two of $R^4$, $R^5$, and $R^6$ are optionally bonded together to form a ring.

An electrophotographic photosensitive member according to the present disclosure includes a conductive substrate and a photosensitive layer. The photosensitive layer contains a charge generating material, a hole transport material, a binder resin, and the above quinone derivative.

DETAILED DESCRIPTION

Figure 1A:
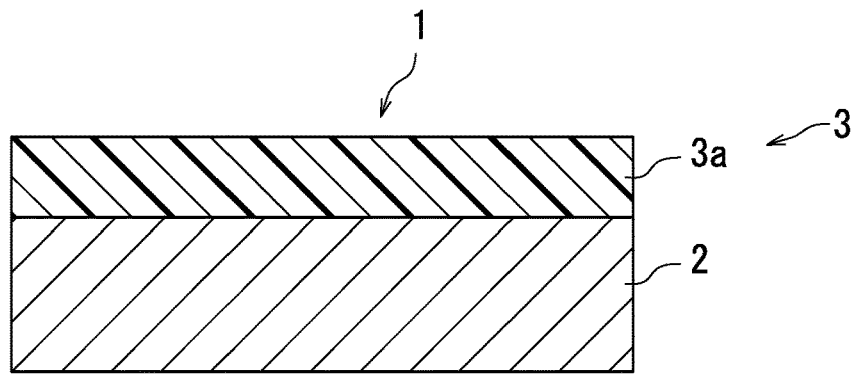
FIGS. 1A, 1B, and 1C each are a schematic cross-sectional view illustrating an example of an electrophotographic photosensitive member according to a second embodiment of the present disclosure.

The following describes embodiments of the present disclosure in detail. However, the present disclosure is in no way limited to the following embodiments. Various alterations may be made to practice the present disclosure within the scope of the aim of the present disclosure. Although explanation is omitted in some places in order to avoid repetition, such omission does not limit the essence of the present disclosure.

In the present description, the term "-based" may be appended to the name of a chemical compound in order to form a generic name encompassing both the chemical compound itself and derivatives thereof. Also, when the term "-based" is appended to the name of a chemical compound used in the name of a polymer, the term indicates that a repeating unit of the polymer originates from the chemical compound or a derivative thereof.

Hereinafter, an alkyl group having 1 to 6 carbon atoms, an alkyl group having 1 to 3 carbon atoms, an alkyl group having 2 to 5 carbon atoms, an alkyl group having 2 to 3 carbon atoms, an alkyl group having 4 to 10 carbon atoms, an alkyl group having 4 to 6 carbon atoms, an alkyl group having 5 to 7 carbon atoms, an aryl group having 6 to 14 carbon atoms, and a cycloalkyl group having 3 to 10 carbon atoms each refer to the following unless otherwise stated.

The alkyl group having 1 to 6 carbon atoms used herein refers to an unsubstituted straight chain or branched chain alkyl group. Examples of the alkyl group having 1 to 6 carbon atoms include a methyl group, an ethyl group, an n-propyl group, an isopropyl group, an n-butyl group, a sec-butyl group, a tert-butyl group, a pentyl group, an isopentyl group, a neopentyl group, and a hexyl group.

The alkyl group having 1 to 3 carbon atoms used herein refers to an unsubstituted straight chain or branched chain alkyl group. Examples of the alkyl group having 1 to 3 carbon atoms include a methyl group, an ethyl group, an n-propyl group, and an isopropyl group.

The alkyl group having 2 to 5 carbon atoms used herein refers to an unsubstituted straight chain or branched chain alkyl group. Examples of the alkyl group having 2 to 5 carbon atoms include an ethyl group, an n-propyl group, an isopropyl group, an n-butyl group, a sec-butyl group, a tert-butyl group, a pentyl group, an isopentyl group, and a neopentyl group.

The alkyl group having 2 to 3 carbon atoms used herein refers to an unsubstituted straight chain or branched chain alkyl group. Examples of the alkyl group having 2 to 3 carbon atoms includes an ethyl group, an n-propyl group, and an isopropyl group.

The alkyl group having 4 to 10 carbon atoms used herein refers to an unsubstituted straight chain or branched chain alkyl group. Examples of the alkyl group having 4 to 10 carbon atoms include an n-butyl group, a sec-butyl group, a tert-butyl group, a pentyl group, an isopentyl group, a neopentyl group, a hexyl group, a heptyl group, an octyl group, a nonyl group, and a decyl group.

The alkyl group having 4 to 6 carbon atoms used herein refers to an unsubstituted straight chain or branched chain alkyl group. Examples of the alkyl group having 4 to 6 carbon atoms include an n-butyl group, a sec-butyl group, a tert-butyl group, a pentyl group, an isopentyl group, a neopentyl group, an isohexyl group, and a hexyl group.

The alkyl group having 5 to 7 carbon atoms used herein refers to an unsubstituted straight chain or branched chain alkyl group. Examples of the alkyl group having 5 to 7 carbon atoms include a pentyl group, an isopentyl group, a neopentyl group, an isohexyl group, an n-hexyl group, and a heptyl group.

The aryl group having 6 to 14 carbon atoms used herein refers to an unsubstituted aryl group. Examples of the aryl group having 6 to 14 carbon atoms include an unsubstituted monocyclic aromatic hydrocarbon having 6 to 14 carbon atoms, an unsubstituted condensed bicyclic aromatic hydrocarbon having 6 to 14 carbon atoms, and an unsubstituted condensed tricyclic aromatic hydrocarbon having 6 to 14 carbon atoms. Examples of the aryl group having 6 to 14 carbon atoms include a phenyl group, a naphthyl group, an anthryl group, and a phenanthryl group.

The cycloalkyl group having 3 to 10 carbon atoms used herein refers to an unsubstituted cycloalkyl group. Examples of the cycloalkyl group having 3 to 10 carbon atoms include a cyclopropyl group, a cyclobutyl group a cyclopentyl group, a cyclohexyl group, a cycloheptyl group, a cyclooctyl group, a cyclononyl group, and a cyclodecyl group.

First Embodiment: Quinone Derivative

[1. Quinone Derivative]

The following describes a quinone derivative according to a first embodiment of the present embodiment. The quinone derivative according to the first embodiment is represented by general formula (1). The quinone derivative represented by general formula (1) may be also referred to below as a quinone derivative (1).

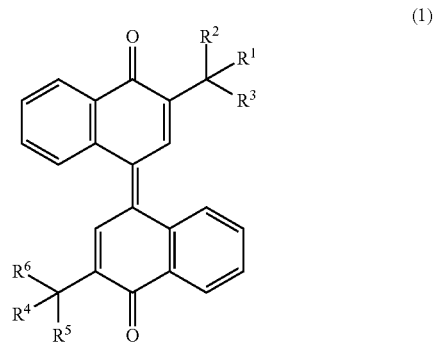

(1)

In general formula (1), at least one of $R^1$, $R^2$, and $R^3$ represents an alkyl group having 4 to 10 carbon atoms or an alkyl group having 2 to 5 carbon atoms that has an aryl group having 6 to 14 carbon atoms. All other of $R^1$, $R^2$ and $R^3$ represents an alkyl group having 1 to 6 carbon atoms, an aryl group having 6 to 14 carbon atoms, or a cycloalkyl group having 3 to 10 carbon atoms. At least two of $R^1$, $R^2$, and $R^3$ are optionally bonded together to form a ring. At least one of $R^4$, $R^5$, and $R^6$ represents an alkyl group having 4 to 10 carbon atoms or an alkyl group having 2 to 5 carbon atoms that has an aryl group having 6 to 14 carbon atoms. All other of $R^4$, $R^5$, and $R^6$ represents an alkyl group having 1 to 6 carbon atoms, an aryl group having 6 to 14 carbon atoms, or a cycloalkyl group having 3 to 10 carbon atoms. At least two of $R^4$, $R^5$, and $R^6$ are optionally bonded together to form a ring.

Use of the quinone derivative (1) according to the first embodiment in a photosensitive member can improve crack resistance of the photosensitive member. The reason therefor may be inferred as below.

At least one of $R^1$, $R^2$, and $R^3$ in the quinone derivative (1) represents an alkyl group having 4 to 10 carbon atoms or an alkyl group having 2 to 5 carbon atoms that has an aryl group having 6 to 14 carbon atoms. Also, at least one of $R^4$, $R^5$, and $R^6$ represents an alkyl group having 4 to 10 carbon atoms or an alkyl group having 2 to 5 carbon atoms that has an aryl group having 6 to 14 carbon atoms. In the above configuration, the quinone derivative (1) has an alkyl group having 4 to 10 carbon atoms or an alkyl group having 2 to 5 carbon atoms that has an aryl group having a 6 to 14 carbon atoms as a substituent. The quinone derivative (1) having a long-chain alkyl group or an aralkyl group is excellent in compatibility with a binder resin. Further, the above substituent, which can function as an anchor, tends to be fixed to a binder resin in a photosensitive layer. Therefore, use of the quinone derivative (1) in a photosensitive member can tend to improve crack resistance of the photosensitive member. A crack resistance evaluation method will be described in detail in Examples.

Description of the quinone derivative (1) according to the first embodiment will be continued. The alkyl group having 4 to 10 carbon atoms, which is represented by any of $R^1$, $R^2$, $R^3$, $R^4$, $R^5$, and $R^6$ in general formula (1), is preferably an alkyl group having 4 to 6 carbon atoms, and more preferably an n-butyl group or an isohexyl group. At least two of $R^1$, $R^2$, and R3 are optionally bonded together to form a ring. At least two of $R^4$, $R^5$, and $R^6$ are optionally bonded together to form a ring. Examples of such rings include a cycloalkylidene group and a cyclic hydrocarbon group. An example of the cycloalkylidene group is a cyclohexylidene group. An example of the cyclic hydrocarbon group is an adamantyl group.

The alkyl group having 5 to 5 carbon atoms that has an aryl group having 6 to 14 carbon atoms, which is represented by any of $R^1$, $R^2$, $R^3$, $R^4$, $R^5$, and $R^6$ in general formula (1), is preferably an alkyl group having 2 to 5 carbon atoms that has a phenyl group, and more preferably a phenylethyl group.

The alkyl group having 1 to 6 carbon atoms, which is represented by any of $R^1$, $R^2$, $R^3$, $R^4$, $R^5$, and $R^6$ in general formula (1), is preferably an alkyl group having 1 to 3 carbon atoms, and more preferably a methyl group.

A preferable aryl group having 6 to 14 carbon atoms, which is represented by any of $R^1$, $R^2$, $R^3$, $R^4$, $R^5$, and $R^6$ in general formula (1), is a phenyl group.

It is preferable in general formula (1) that at least one of $R^1$, $R^2$, and $R^3$ represents an alkyl group having 4 to 6 carbon atoms or an alkyl group having 2 to 5 carbon atoms that has a phenyl group and all other of $R^1$, $R^2$, and $R^3$ represents an alkyl group having 1 to 3 carbon atoms. It is also preferable that at least one of $R^4$, R5, and $R^6$ represents an alkyl group having 4 to 6 carbon atoms or an alkyl group having 2 to 5 carbon atoms that has a phenyl group and all other of $R^4$, $R^5$, and $R^6$ represents an alkyl group having 1 to 3 carbon atoms.

It is preferable in terms of improving crack resistance of a photosensitive member that one or two of $R^1$, $R^2$, and $R^3$ in general formula (1) each represent an alkyl group having 2 to 3 carbon atoms that has a phenyl group or an alkyl group having 5 to 7 carbon atoms and all other of $R^1$, $R^2$, and $R^3$ represents a methyl group. Preferably, at least two of $R^1$, $R^2$, and $R^3$ are not bonded together to form a ring. It is preferable that one or two of $R^4$, $R^5$, and $R^6$ each represent an alkyl group having 1 to 3 carbon atoms that has a phenyl group or an alkyl group having 1 to 5 carbon atoms and no greater than 7 and all other of $R^4$, $R^5$, and $R^6$ represents a methyl group. Preferably, at least two of $R^4$, $R^5$, and $R^6$ are not bonded together to form a ring.

Specific examples of the quinone derivative (1) include quinone derivatives represented by respective chemical formulae (1-1)-(1-7) (also referred to below as quinone derivatives (1-1)-(1-7), respectively).

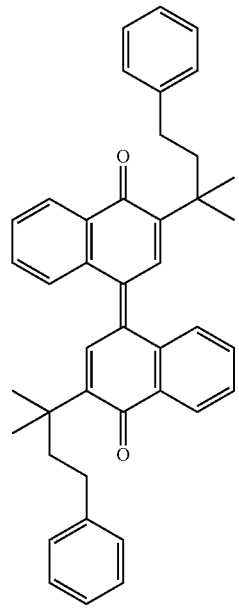

(1-1)

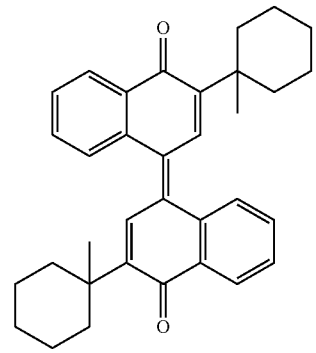

(1-2)

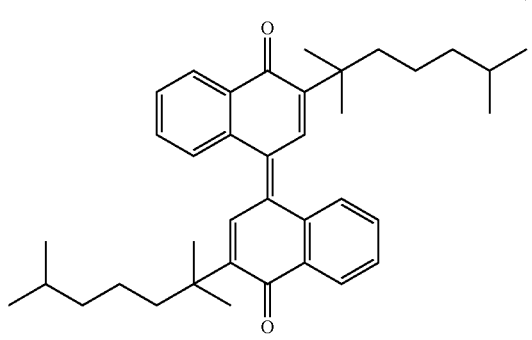

(1-3)

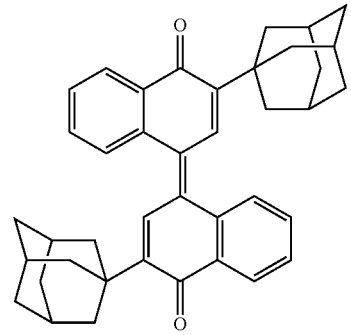

(1-4)

-continued (1-5)

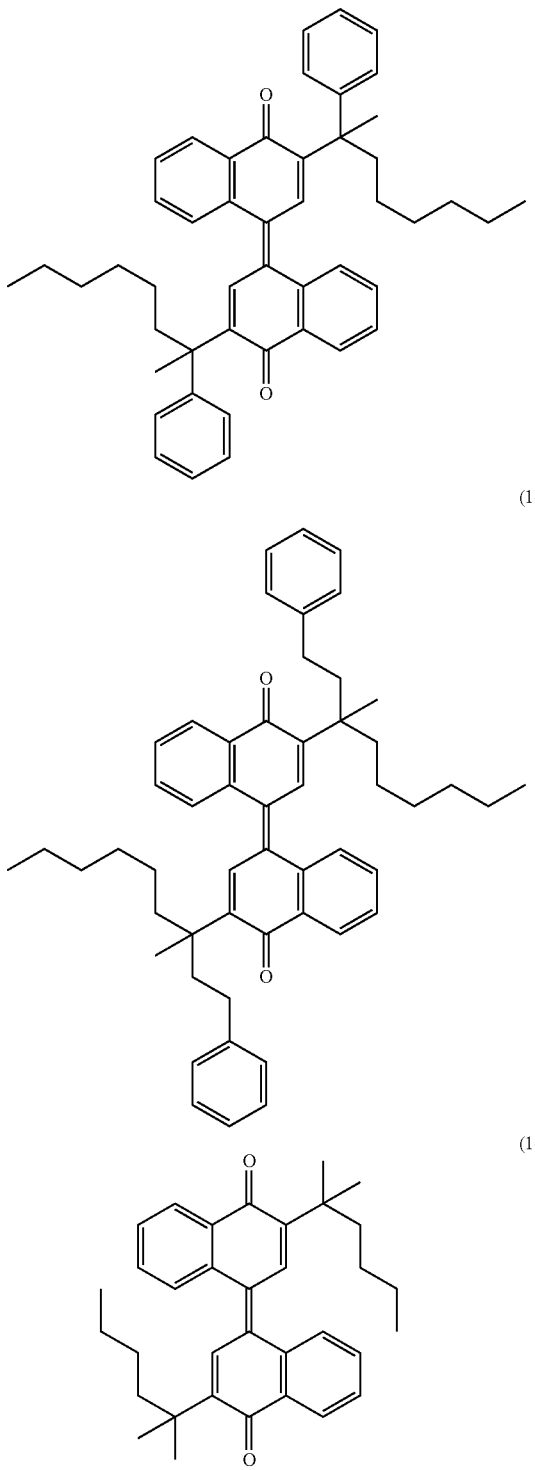

(1-6)

(1-7)

The quinone derivatives (1-1)-(1-6) are preferable among the quinone derivatives (1-1)-(1-7) in terms of further improving crack resistance of a photosensitive member, and the quinone derivatives (1-1), (1-3), and (1-5) are more preferable.

The quinone derivatives (1-1)-(1-3), (1-6) and (1-7) are preferable among the quinone derivatives (1-1)-(1-7) in terms of improving sensitivity characteristics of a photosensitive member, and the quinone derivatives (1-1) and (1-6) are more preferable.

[2. Method for Producing Quinone Derivative (1)]

The quinone derivative (1) is produced for example through a reaction represented by reaction formula (R-1) (also referred to below as a Reaction (R-1)), a reaction represented by reaction formula (R-2) (also referred to below as a Reaction (R-2)), and a reaction represented by reaction formula (R-3) (also referred to below as a Reaction (R-3)) or through a method conforming therewith. The method for producing the quinone derivative (1) includes for example causing Reaction (R-1), Reaction (R-2), and Reaction (R-3).

$R^1$, $R^2$, and $R^3$ in Reaction (R-1) are the same as $R^1$, $R^2$, and $R^3$ in general formula (1), respectively.

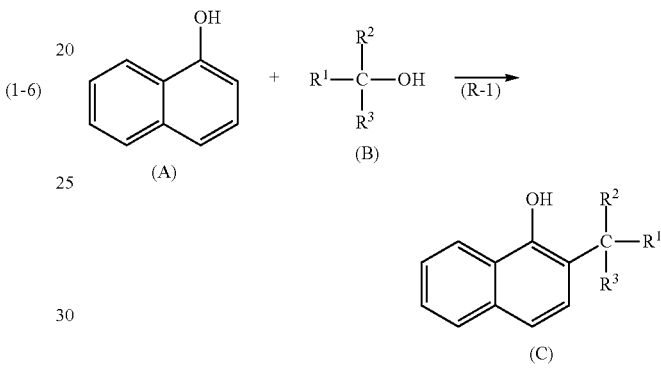

In Reaction (R-1), 1 mole equivalent of a compound (1-naphthol) represented by chemical formula (A) and 1 mole equivalent of a compound (alcohol derivative) represented by general formula (B) (also referred to below as an alcohol derivative (B)) are caused to react together in the presence of a concentrated sulfuric acid in a solvent to yield 1 mole equivalent of a compound represented by general formula (C) (also referred to below as a naphthol derivative (C)) that is an intermediate. In Reaction (R-1), at least 1 mole and no greater than 2.5 moles of the alcohol derivative (B) is preferably added relative to 1 mole of 1-naphthol. Percentage yield of the naphthol derivative (C) can be easily increased by adding at least 1 mole of the alcohol derivative (B) relative to 1 mole of 1-naphthol. By contrast, when 2.5 or less moles of the alcohol derivative (B) is added relative to 1 mole of 1-naphthol, non-reacted alcohol derivative (B) hardly remains after Reaction (R-1). This can facilitate purification of the quinone derivative (1). Reaction (R-1) is preferably carried out at room temperature (for example, 25° C.). Reaction (R-1) preferably has a reaction time of at least 1 hour and no greater than ten hours. Reaction (R-1) can be carried out in a solvent. Examples of the solvent include organic acid solutions (for example, acetic acid).

More specifically, 1-naphthol and the alcohol derivative (B) are caused to react together in Reaction (R-1). After Reaction (R-1), ion exchanged water is added to a resultant reaction liquid and a product by Reaction (R-1) is extracted to an organic layer. An example of the organic solvent is chloroform. An alkaline aqueous solution is added to the organic layer to wash the organic layer for notarization. Examples of the alkaline includes hydroxides of alkali metals (specific examples include sodium hydroxide and potassium hydroxide) and hydroxides of alkali earth metals (a specific example is calcium hydroxide).

$R^4$, $R^5$, and $R^6$ in Reaction (R-2) are the same as $R^4$, $R^5$, and $R^6$ in general formula (1), respectively.

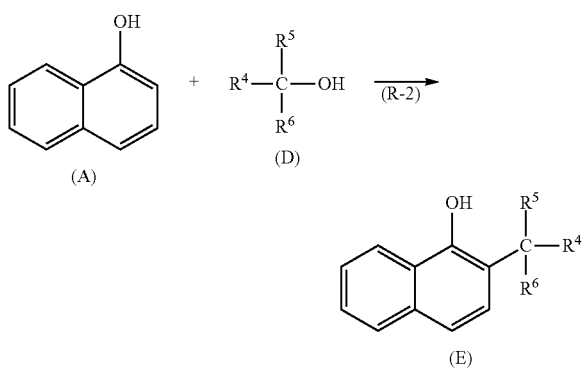

In Reaction (R-2), 1 mole equivalent of the compound represented by chemical formula (A) (1-naphthol) and 1 mole equivalent of a compound (alcohol derivative) represented by general formula (D) (also referred to below as an alcohol derivative (D)) are caused to react together in the presence of concentrated sulfuric acid in the solvent to yield 1 mole equivalent of a compound represented by general formula (E) (also referred to below as a naphthol derivative (E)) that is an intermediate. Reaction (R-2) is the same reaction as Reaction (R-1) other than that the alcohol derivative (B) is changed to the alcohol derivative (D).

$R^1$, $R^2$, $R^3$, $R^4$, $R^5$, and $R^6$ in Reaction (R-3) are the same as $R^1$, $R^2$, $R^3$, $R^4$, $R^5$, and $R^6$ in general formula (1), respectively.

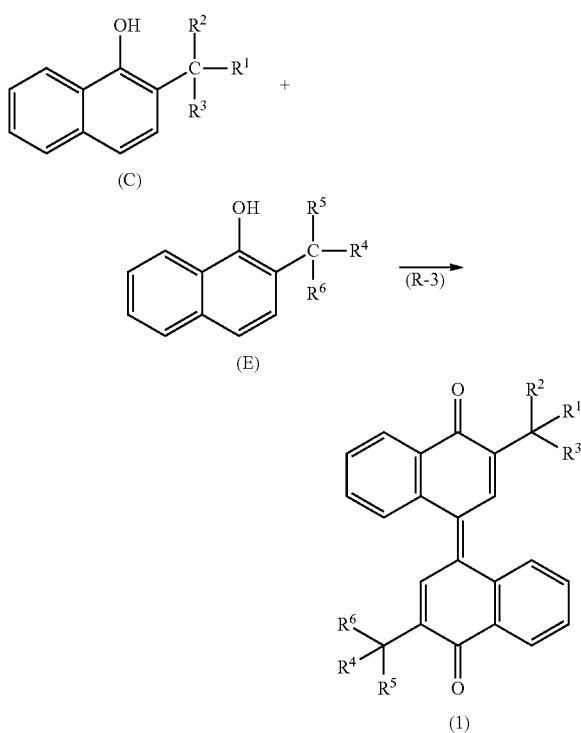

In Reaction (R-3), 1 mole equivalent of the naphthol derivative (C) and 1 mole equivalent of the naphthol derivative (E) are caused to react together in the presence of an oxidant and a solvent to yield 1 mole equivalent of the quinone derivative (1). It is preferable to add 1 mole of the oxidant relative to 1 mole of the naphthol derivative (C) and 1 mole of the naphthol derivative (E) in Reaction (R-3). Examples of the oxidant include chloranil, potassium permanganate, and silver oxide. Reaction (R-3) is preferably carried out at room temperature (for example, 25° C.). Reaction (R-3) preferably has a reaction time of at least one hour and no greater than ten hours. Examples of the solvent include chloroform and dichloromethane.

The method for producing the quinone derivative (1) may include any additional processes depending on necessity thereof. A purification process is an example of the additional process. A purification method may be any known method (specific examples include filtration, chromatography, and crystallization).

Second Embodiment: Electrophotographic Photosensitive Member

The following describes an electrophotographic photosensitive member (also referred to below as a photosensitive member) according to a second embodiment of the present disclosure. The photosensitive member includes a conductive substrate and a photosensitive layer. Examples of the photosensitive member include a single-layer electrophotographic photosensitive member (also referred to below as a single-layer photosensitive member) and a multi-layer electrophotographic photosensitive member (also referred to below as multi-layer photosensitive member).

[1. Single-Layer Photosensitive Member]

Figure 1B:
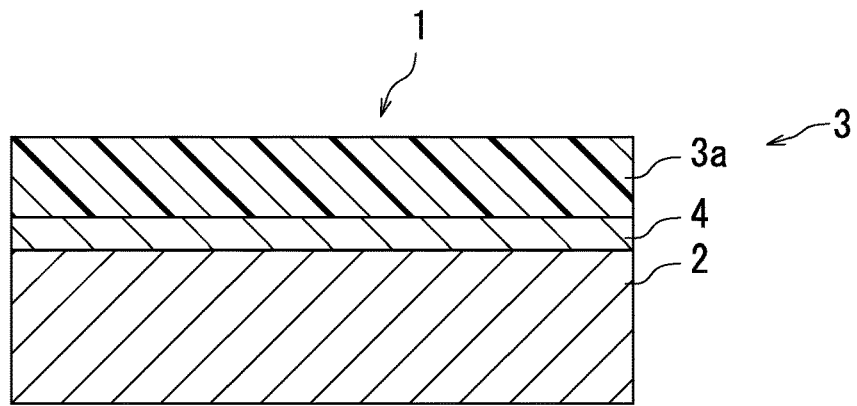
Figure 1C:
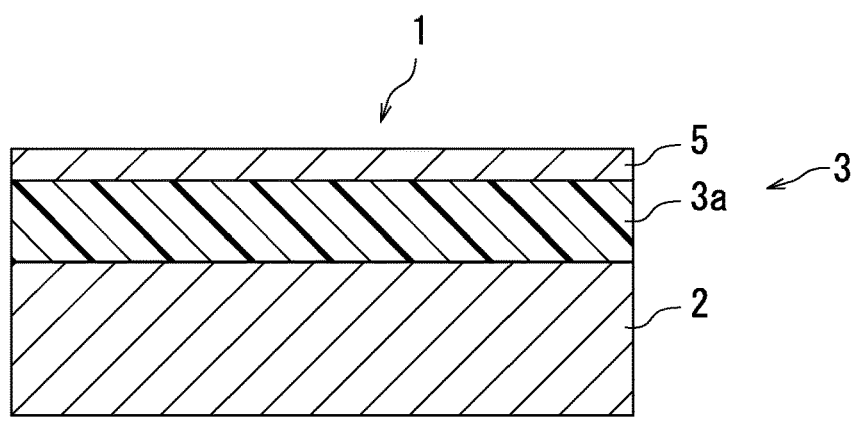

Configurations of the single-layer photosensitive member will be described below with reference to FIGS. 1A-1C. FIGS. 1A-1C illustrate the configurations of respective single-layer photosensitive members that each are an example of a photosensitive member 1 according to the second embodiment.

The photosensitive members 1 in FIGS. 1A-1C each are a single-layer photosensitive member. As illustrated in FIG. 1A, the single-layer photosensitive member includes for example a conductive substrate 2 and a photosensitive layer 3. The photosensitive layer 3 of the single-layer photosensitive member includes a single-layer photosensitive layer 3a. The single-layer photosensitive layer 3a is a photosensitive layer 3 that is a single layer.

As illustrated in FIG. 1B, the single-layer photosensitive member that is the photosensitive member 1 may include an intermediate layer (undercoat layer) 4 in addition to the conductive substrate 2 and the single-layer photosensitive layer 3a. The intermediate layer 4 is disposed between the conductive substrate 2 and the single-layer photosensitive layer 3a. Alternatively, a protective layer 5 may be disposed on the single-layer photosensitive layer 3a, as illustrated in FIG. 1C.

No particular limitations are placed on thickness of the single-layer photosensitive layer 3a, so long as the thickness thereof is sufficient to enable the single-layer photosensitive layer 3a to function as a single-layer photosensitive layer. The single-layer photosensitive layer 3a preferably has a thickness of at least 5 μm and no greater than 100 μm, and more preferably at least 10 μm and no greater than 50 μm.

[2. Multi-Layer Photosensitive Member]

Figure 2A:
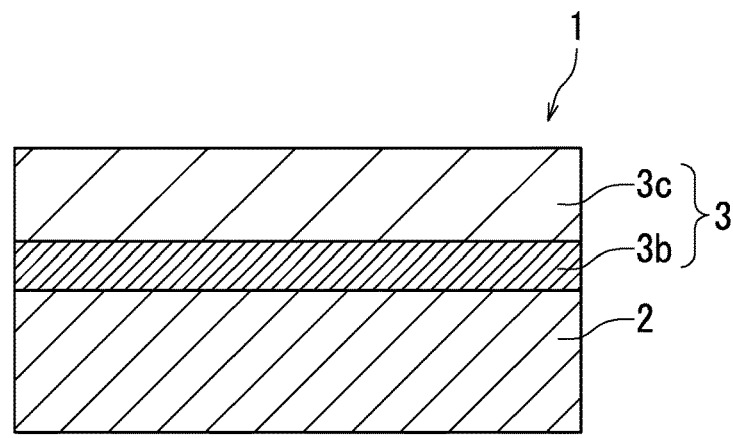
FIGS. 2A, 2B, and 2C each are a schematic cross-sectional view illustrating another example of the electrophotographic photosensitive member according to the second embodiment of the present disclosure.
Figure 2B:
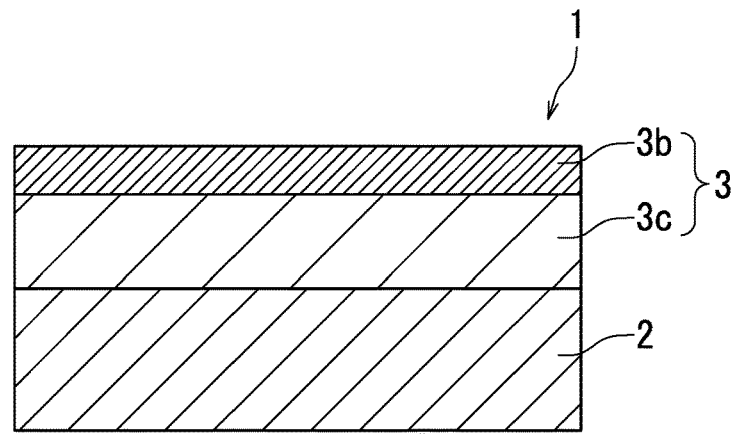
Figure 2C:
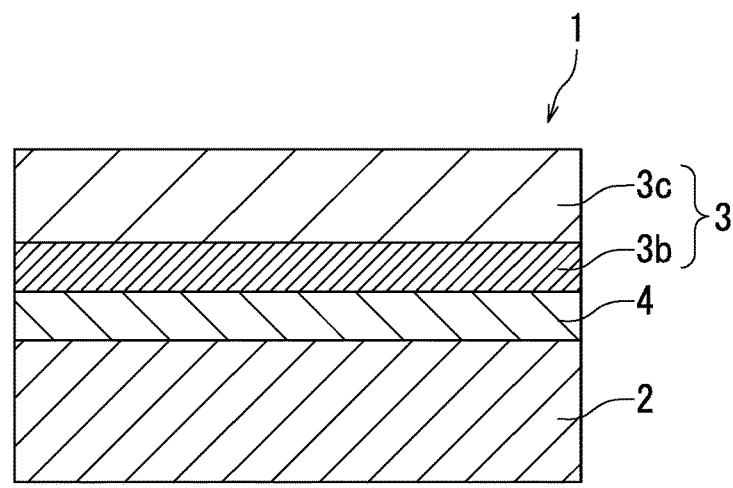

The multi-layer photosensitive member includes a photosensitive layer 3 that includes a charge generating layer 3c and a charge transport layer 3b. Configurations of the multi-layer photosensitive member will be described below with reference to FIGS. 2A-2C. FIGS. 2A-2C illustrate the configurations of respective multi-layer photosensitive members that each are an example of the photosensitive member 1 according to the second embodiment.

The respective photosensitive members 1 in FIGS. 2A-2C each are a multi-layer photosensitive member. As illustrated in FIG. 2A, the multi-layer photosensitive member that is the photosensitive member 1 includes for example a conductive substrate 2 and a photosensitive layer 3. The photosensitive layer 3 includes a charge generating layer 3b and a charge transport layer 3c. As illustrated in FIG. 2B, it is possible that the charge transport layer 3c is disposed on the conductive substrate 2 and the charge generating layer 3b is disposed on the charge transport layer 3c in the multi-layer photosensitive member. It is preferable that the charge generating layer 3b is disposed on the conductive substrate 2 and the charge transport layer 3c is disposed on the charge generating layer 3b, as illustrated in FIG. 2A, in order to improve abrasion resistance of the multi-layer photosensitive member.

As illustrated in FIG. 2C, the multi-layer photosensitive member may include an intermediate layer (undercoat layer) 4 in addition to the conductive substrate 2 and the photosensitive layer 3. The intermediate layer 4 is disposed between the conductive substrate 2 and the photosensitive layer 3. Furthermore, a protective layer 5 (see FIG. 1C) may be disposed on the photosensitive layer 3.

No particular limitations are placed on respective thicknesses of the charge generating layer 3b and the charge transport layer 3c, so long as the thicknesses thereof are sufficient to enable the charge generating layer 3b and the charge transport layer 3c to implement their respective functions. The charge generating layer 3b preferably has a thickness of at least 0.01 μm and no greater than 5 μm, and more preferably at least 0.1 μm and no greater than 3 μm. The charge transport layer 3c preferably has a thickness of at least 2 μm and no greater than 100 μm, and more preferably at least 5 μm and no greater than 50 μm.

The photosensitive member 1 according to the second embodiment includes the photosensitive layer 3. The photosensitive layer 3 contains a charge generating material, a hole transport material, a binder resin, and the quinone derivative (1). In a configuration in which the photosensitive member 1 is a single-layer photosensitive member, the single-layer photosensitive layer contains for example the charge generating material, the hole transport material, the binder resin, and the quinone derivative (1) that serves as an electron transport material. In a configuration in which the photosensitive member 1 is a multi-layer photosensitive member, the charge generating layer 3c of the multi-layer photosensitive layer contains for example the charge generating material and a binder resin for use in a charge generating material (also referred to below as a base resin). The charge transport layer of the multi-layer photosensitive member contains for example the hole transport material, the binder resin, and the quinone derivative (1) that serves as an electron acceptor compound. An additive may be contained in the single-layer photosensitive layer in a configuration in which the photosensitive member 1 is a single-layer photosensitive member and in the charge generating layer 3b and the charge transport layer 3c in a configuration in which the photosensitive member 1 is a multi-layer photosensitive member. Description will be made below about the conductive substrate 2, the electron transport material, the electron acceptor compound, the hole transport material, the charge generating material, the binder resin, the base resin, the additive, and the intermediate layer 4 that each are an element or a component of the photosensitive member 1. A photosensitive member production method will be described also.

[3. Conductive Substrate]

No particular limitations are placed on the conductive substrate other than being a conductive substrate that can be used in a photosensitive member. It is only required that at least a surface portion of the conductive substrate is made from a conductive material. An example of the conductive substrate is a conductive substrate made from a conductive material. Another example of the conductive substrate is a substrate covered with a conductive material. Examples of the conductive material include aluminum, iron, copper, tin, platinum, silver, vanadium, molybdenum, chromium, cadmium, titanium, nickel, palladium, and indium. Any one of the conductive materials listed above may be used or a combination of any two or more of the conductive materials listed above may be used. Examples of the combination of two or more conductive materials include alloys (specific examples include an aluminum alloy, stainless steel, and brass). Among the conductive materials listed above, aluminum or an aluminum alloy is preferable in terms of good movement of charge from the photosensitive layer to the conductive substrate.

The conductive substrate has a shape that is appropriately selected according to configuration of an image forming apparatus. Examples of the shape of the conductive substrate include a sheet-like shape and a drum-like shape. The conductive substrate has a thickness that is appropriately selected according to the shape of the conductive substrate.

[4. Electron Transport Material and Electron Acceptor Compound]

As described above, the single-layer photosensitive layer of the single-layer photosensitive member contains the quinone derivative (1) as an electron transport material. The charge transport layer of the multi-layer photosensitive member contains the quinone derivative (1) as an electron acceptor compound. In a configuration in which the photosensitive layer contains the quinone derivative (1), the photosensitive member in the second embodiment is excellent in crack resistance.

In a configuration in which the photosensitive member is a single-layer photosensitive member, the amount of the quinone derivative (1) is preferably at least 10 parts by mass and no greater than 200 parts by mass relative to 100 parts by mass of the binder resin contained in the single-layer photosensitive layer, more preferably at least 10 parts by mass and no greater than 100 parts by mass, and particularly preferably at least 10 parts by mass and no greater than 75 parts by mass.

In a configuration in which the photosensitive member is a multi-layer photosensitive member, the amount of the quinone derivative (1) is preferably at least 10 parts by mass and no greater than 200 parts by mass relative to 100 parts by mass of the binder resin contained in the charge transport layer, and more preferably at least 20 parts by mass and no greater than 100 parts by mass.

The single-layer photosensitive layer may further contain another electron transport material in addition to the quinone derivative (1). The charge transport layer may further contain another electron acceptor compound in addition to the quinone derivative (1). Examples of the other electron transport material and the other electron acceptor compound include quinone-based compounds (quinone-based compounds other than the quinone derivative (1)), diimide-based compounds, hydrazone-based compounds, malononitrile-based compounds, thiopyran-based compounds, trinitrothioxanthone-based compounds, 3,4,5,7-tetranitro-9-fluorenone-based compounds, dinitroanthracene-based compounds, dinitroacridine-based compounds, tetracyanoethylene, 2,4,8-trinitrothioxanthone, dinitrobenzene, dinitroacridine, succinic anhydride, maleic anhydride, and dibromomaleic anhydride. Examples of the quinone-based compounds include diphenoquinone-based compounds, azoquinone-based compounds, anthraquinone-based compounds, naphthoquinone-based compounds, nitroanthraquinone-based compounds, and dinitroanthraquinone-based compounds. Any one of the electron transport materials or the electron acceptor compounds listed above may be used or a combination of any two or more of the electron transport materials or the electron acceptor compounds listed above may be used.

[5. Hole Transport Material]

In a configuration in which the photosensitive member is a single-layer photosensitive member, the single-layer photosensitive layer contains a hole transport material. In a configuration in which the photosensitive member is a multi-layer photosensitive member, the charge transport layer may contain a hole transport material. Examples of the hole transport material that can be used include nitrogen containing cyclic compounds and condensed polycyclic compounds. Examples of the nitrogen containing cyclic compounds and the condensed polycyclic compounds include diamine derivatives (specific examples include a benzidine derivative, an N,N,N',N'-tetraphenylphenylenediamine derivative, N,N,N',N'-tetraphenylnaphtylenediamine derivative, and an N,N,N',N'-tetraphenylphenanthrylenediamine derivative), oxadiazole-based compounds (specifics examples include 2,5-di(4-methylaminophenyl)-1,3,4-oxadiazole), styryl compounds (a specific example is 9-(4-diethylaminostyryl)anthracene), carbazole compounds (a specific example is polyvinyl carbazole), organic polysilane compounds, pyrazoline-based compounds (a specific example is 1-phenyl-3-(p-dimethylaminophenyl)pyrazoline), hydrazone-based compounds, indole-based compounds, oxazole-based compounds, isoxazole-based compounds, thiazole-based compounds, thiadiazole-based compounds, imidazole-based compounds, pyrazole-based compounds, and triazole-based compounds. Any one of the electron transport materials listed above may be used or a combination of any two or more of the electron transport materials listed above may be used. A compound represented by general formula (2) (benzidine derivative) is preferable among the hole transport materials listed above.

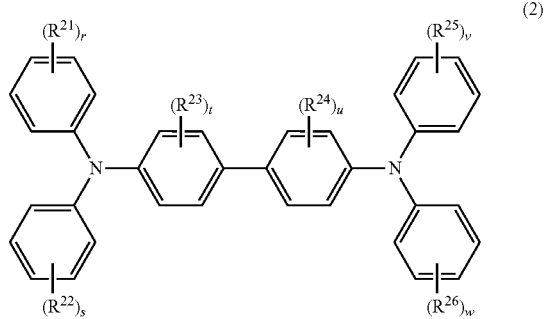

In general formula (2), $R^{21}$, $R^{22}$, $R^{23}$, $R^{24}$, $R^{25}$, and $R^{26}$ each represent, independently of one another, an alkyl group having 1 to 6 carbon atoms or an alkoxy group having 1 to 6 carbon atoms. Subscripts r, s, v, and w each represent, independently of one another, an integer of at least 0 and no greater than 5. Subscripts t and u each represent, independently of one another, an integer of at least 0 and no greater than 4.

$R^{21}$-$R^{26}$ in general formula (2) each preferably represent, independently of one another, an alkyl group having 1 to 6 carbon atoms, more preferably an alkyl group having 1 to 3 carbon atoms, and further preferably a methyl group. Subscripts r, s, v, w, t, and u preferably represents 1.

The compound represented by general formula (2) is preferably a compound represented by chemical formula (H-1) (also referred to below as a compound (H-1)).

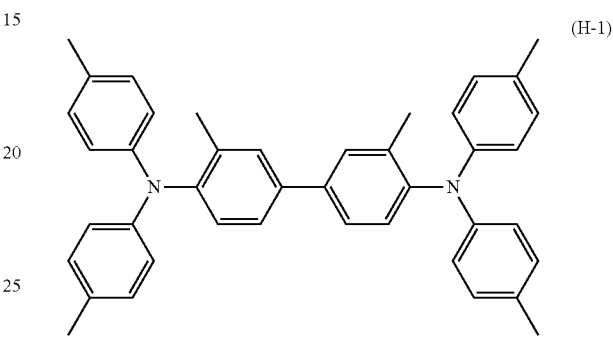

In a configuration in which the photosensitive member is a single-layer photosensitive member, the amount of the hole transport material is preferably at least 10 parts by mass and no greater than 200 parts by mass relative to 100 parts by mass of the binder resin contained in the single-layer photosensitive layer, more preferably at least 10 parts by mass and no greater than 100 parts by mass, and particularly preferably at least 10 parts by mass and no greater than 75 parts by mass.

In a configuration in which the photosensitive member is a multi-layer photosensitive member, the amount of the hole transport material is preferably at least 10 parts by mass and no greater than 200 parts by mass relative to 100 parts by mass of the binder resin contained in the charge transport layer, and more preferably at least 20 parts by mass and no greater than 100 parts by mass.

[6. Charge Generating Material]

In a configuration in which the photosensitive member is a single-layer photosensitive member, the single-layer photosensitive layer contains a charge generating material. In a configuration in which the photosensitive member is a multi-layer photosensitive member, the charge generating layer contains a charge generating material.

No particular limitations are placed on the charge generating material other than being a charge generating material that can be used in a photosensitive member. Examples of the charge generating material include phthalocyanine-based pigments, perylene-based pigments, bisazo pigments, tris-azo pigments, dithioketopyrrolopyrrole pigments, metal-free naphthalocyanine pigments, metal naphthalocyanine pigments, squaraine pigments, indigo pigments, azulenium pigments, cyanine pigments, powders of inorganic photoconductive materials (specific examples include selenium, selenium-tellurium, selenium-arsenic, cadmium sulfide, and amorphous silicon), pyrylium pigments, anthanthrone-based pigments, triphenylmethane-based pigments, threne-based pigments, toluidine-based pigments, pyrazoline-based pigments, and quinacridon-based pigments. Any one of the charge generating materials listed above may be used or a combination of any two or more of the charge generating materials listed above may be used.

Examples of the phthalocyanine-based pigments include metal phthalocyanines and a metal-free phthalocyanine represented by chemical formula (C-1) (also referred to below as a compound (C-1)). Examples of the metal phthalocyanines include hydroxygallium phthalocyanine, chlorogallium phthalocyanine, and a titanyl phthalocyanine represented by chemical formula (C-2) (also referred to below as a compound (C-2)). A phthalocyanine-based pigment used as the charge generating material may be crystalline or non-crystalline. No particular limitations are placed on the crystal structure (for example, X-form, α-form, β-form, Y-form, V-form, and II-form) of the phthalocyanine-based pigment, and a phthalocyanine-based pigment having any type of crystal structure can be used.

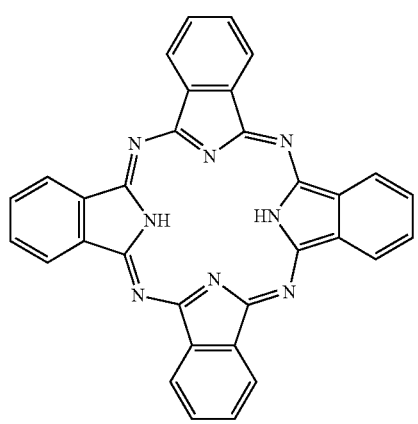

(C-1)

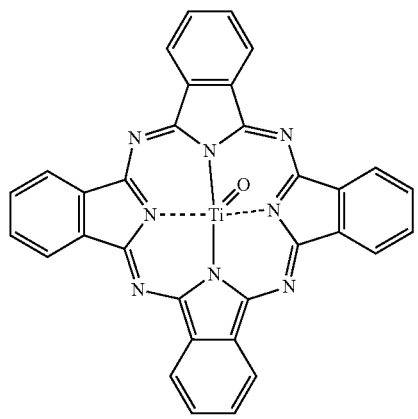

(C-2)

An example of crystalline metal-free phthalocyanine is metal-free phthalocyanine having a crystal structure of X form (also referred to below as X-form metal-free phthalocyanine). Examples of crystalline titanyl phthalocyanine include titanyl phthalocyanines each having a crystal structure of α-form, β-form, or Y-form (also referred to below as α-form titanyl phthalocyanine, β-form titanyl phthalocyanine, and Y-form titanyl phthalocyanine, respectively). An example of crystalline hydroxygallium phthalocyanine is hydroxygallium phthalocyanine having a crystal structure of V-form. An example of crystalline chlorogallium phthalocyanine is chlorogallium phthalocyanine having a crystal structure of II-form.

For example, a photosensitive member having sensitivity in a wavelength range of at least 700 nm is preferably used in a digital optical image forming apparatus. Examples of the digital optical image forming apparatus include a laser beam printer and a facsimile machine that each use a light source such as a semiconductor laser. The phthalocyanine-based pigments, which have high quantum yield in a wavelength range of at least 700 nm, are preferable as the charge generating material, and metal-free phthalocyanine and titanyl phthalocyanine are more preferable. An X-form metal-free phthalocyanine and a Y-form titanyl phthalocyanine are further preferable as the charge generating material in order to improve electrical properties of a photosensitive member in a configuration in which the photosensitive layer contains the quinone derivative (1). The charge generating material preferably contains an X-form metal-free phthalocyanine or a Y-form titanyl phthalocyanine in order to improve crack resistance in a configuration in which the photosensitive layer contains the quinone derivative (1), and an X-form metal-free phthalocyanine is more preferable.

Y-form titanyl phthalocyanine crystals exhibit a main peak at a Bragg angle (2θ±0.2° of 27.2°) in a CuKα characteristic X-ray diffraction spectrum. The term, main peak in a CuKα characteristic X-ray diffraction spectrum refers to a most intense or second most intense peak within a range of Bragg angles (2θ±0.2°) from 3° to 40° in the CuKα characteristic X-ray diffraction spectrum.

(CuKα Characteristic X-Ray Diffraction Spectrum Measuring Method)

The following describes an example of a CuKα characteristic X-ray diffraction spectrum measuring method. A sample (titanyl phthalocyanine crystals) is loaded into a sample holder of an X-ray diffraction spectrometer (for example, "RINT (registered Japanese trademark) 1100" produced by Rigaku Corporation) and an X-ray diffraction spectrum is measured using a Cu X-ray tube, a tube voltage of 40 kV, a tube current of 30 mA, and CuKα characteristic X-rays having a wavelength of 1.542 Å. The CuKα characteristic X-ray diffraction spectrum is measured for example in a range (2θ) of at least 3° and no greater than 40° (starting angle: 3°, stop angle: 40°). The scanning speed is for example 10°/min.

An anthanthrone-based pigment is favorably used as the charge generating material of a photosensitive member adopted in an image forming apparatus using a short-wavelength laser light source. The short-wavelength laser light source emits short-wavelength laser light for example having a wavelength of at least 350 nm and no greater than 550 nm.

In a configuration in which the photosensitive member is a single-layer photosensitive member, the amount of the charge generating material is preferably at least 0.1 parts by mass and no greater than 50 parts by mass relative to 100 parts by mass of the binder resin contained in the single-layer photosensitive layer, more preferably at least 0.5 parts by mass and no greater than 30 parts by mass, and particularly preferably at least 0.5 parts by mass and no greater than 4.5 parts by mass.

In a configuration in which the photosensitive member is a multi-layer photosensitive member, the amount of the charge generating material is preferably at least 5 parts by mass and no greater than 1,000 parts by mass relative to 100 parts by mass of the base resin contained in the charge generating layer of the multi-layer photosensitive member, and more preferably at least 30 parts by mass and no greater than 500 parts by mass.

[7. Binder Resin]

Examples of the binder resin include thermoplastic resins, thermosetting resins, and photocurable resins. Examples of the thermoplastic resins include polycarbonate resins, polyarylate resins, styrene-butadiene-based resins, styrene-acrylonitrile resins, styrene-maleic acid resins, acrylic acid-based resins, styrene-acrylic acid resins, polyethylene resins, ethylene-vinyl acetate resins, chlorinated polyethylene resins, polyvinyl chloride resins, polypropylene resins, ionomer resins, vinyl chloride-vinyl acetate resins, alkyd resins, polyamide resins, urethane resins, polysulfone resins, diallyl phthalate resins, ketone resins, polyvinyl butyral resins, polyester resins, and polyether resins. Examples of the thermosetting resins include silicone resins, epoxy resins, phenolic resins, urea resins, and melamine resins. Examples of the photocurable resins include epoxy-acrylic acid-based resins (specific examples include acrylic acid derivative adducts of epoxy compounds) and urethane-acrylic acid-based resins (specific examples include acrylic acid derivative adducts of urethane compounds). Any one of the binder resins listed above may be used or a combination of any two or more of the binder resins listed above may be used.

Among the binder resins listed above, polycarbonate resins are preferable for obtaining a single-layer photosensitive layer and a charge transport layer having excellent balance in terms of processability, mechanical properties, optical properties, and abrasion resistance. Examples of the polycarbonate resins include a bisphenol Z polycarbonate resin represented by the following chemical formula (Resin-1) (also referred to below as a Z polycarbonate resin (Resin-1)), bisphenol ZC polycarbonate resins, bisphenol C polycarbonate resins, and bisphenol A polycarbonate resins. The Z polycarbonate resin (Resin-1) is preferable in terms of excellent compatibility with the quinone derivative (1) and improving dispersibility of the quinone derivative (1) in a photosensitive layer.

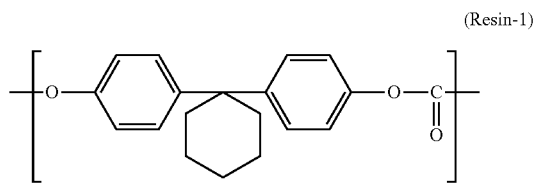

(Resin-1)

In terms of viscosity average molecular weight, the binder resin preferably has a viscosity average molecular weight of at least 40,000, and more preferably at least 40,000 and no greater than 52,500. As a result of the viscosity average molecular weight of the binder resin being at least 40,000, abrasion resistance of the photosensitive member can be improved more easily. As a result of the viscosity average molecular weight of the binder resin being no greater than 52,500, the binder resin dissolves more readily in a solvent in formation of the photosensitive layer and viscosity of an application liquid for charge transport layer formation or an application liquid for single-layer photosensitive layer formation is not excessively high. Formation of the charge transport layer or the single-layer photosensitive layer can accordingly be facilitated.

[8. Base Resin]

In a configuration in which the photosensitive member is a multi-layer photosensitive member, the charge generating layer of the photosensitive member contains a base resin. No particular limitations are placed on the base resin, so long as the base resin is adoptable in the photosensitive member. Examples of the base resin include thermoplastic resins, thermosetting resins, and photocurable resins. Examples of the thermoplastic resins include styrene-butadiene-based resins, styrene-acrylonitrile resins, styrene-maleic acid resins, styrene-acrylic acid resins, acrylic acid-based resins, polyethylene resins, ethylene-vinyl acetate resins, chlorinated polyethylene resins, polyvinyl chloride resins, polypropylene resins, ionomer, vinyl chloride-vinyl acetate resins, alkyd resins, polyamide resins, urethane resins, polycarbonate resins, polyarylate resins, polysulfone resins, diallyl phthalate resins, ketone resins, polyvinyl butyral resins, polyether resins, and polyester resins. Examples of the thermosetting resins include silicone resins, epoxy resins, phenolic resins, urea resins, melamine resins, and other crosslinkable thermosetting resins. Examples of the photocurable resins include epoxy-acrylic acid-based resins (specific examples include acrylic acid derivative adducts of epoxy compounds) and urethane-acrylic acid-based resins (specific examples include acrylic acid derivative adducts of urethane compounds). Any one of the base resins listed above may be used or a combination of any two or more of the base resins listed above may be used.

The base resin contained in the charge generating layer is preferably different from the binder resin contained in the charge transport layer. The reason for the above is that the charge generating layer is inhibited from dissolving in a solvent of the application liquid for charge transport layer formation. The multi-layer photosensitive member is typically produced by forming the charge generating layer on the conductive substrate followed by formation of the charge transport layer on the charge generating layer. The reason for the above is that the application liquid for charge transport layer formation is applied onto the charge generating layer in formation of the charge transport layer.

[9. Additives]

The photosensitive layer (charge generating layer, charge transport layer, or single-layer photosensitive layer) of the photosensitive member may optionally contain various additives depending on necessity thereof. Examples of the additive include antidegradants (specific examples include an antioxidant, a radical scavenger, a quencher, and a ultraviolet absorbing agent), softeners, surface modifiers, extenders, thickeners, dispersion stabilizers, waxes, donors, surfactants, plasticizers, sensitizers, and leveling agents.

[10. Intermediate Layer]

The intermediate layer (undercoat layer) contains for example inorganic particles and a resin (intermediate layer resin). It is thought that provision of the intermediate layer facilitates flow of current generated when the photosensitive member is exposed to light and inhibits increasing resistance, while also maintaining insulation to a sufficient degree so as to inhibit occurrence of leakage current.

Examples of the inorganic particles include particles of metals (specific examples include aluminum, iron, and copper), particles of metal oxides (specific examples include titanium oxide, alumina, zirconium oxide, tin oxide, and zinc oxide), and particles of non-metal oxides (a specific example is silica). Any one type of the inorganic particles listed above may be used or a combination of any two or more types of the organic particles listed above may be used.

No particular limitations are placed on the intermediate layer resin other than being a resin that can be used to form the intermediate layer. The intermediate layer may optionally contain various additives depending on necessity thereof. The additives are the same as the additives that can be contained in the photosensitive layer.

[11. Photosensitive Member Production Method]

In a configuration in which the photosensitive member is a single-layer photosensitive member, the single-layer photosensitive member is produced for example as follows. The single-layer photosensitive member is produced by applying an application liquid for single-layer photosensitive layer formation onto the conductive substrate and drying the application liquid thereon. The application liquid for single-layer photosensitive layer formation is prepared by dissolving or dispersing an electron transport material, a charge generating material, a hole transport material, a binder resin, and a component to be added depending on necessity thereof (for example, an additive) in a solvent.

In a configuration in which the photosensitive member is a multi-layer photosensitive member, the multi-layer photosensitive member is produced for example as follows. An application liquid for charge generating layer formation and an application liquid for charge transport layer formation are prepared first. The application liquid for charge generating layer formation is applied onto the conductive substrate and dried to form a charge generating layer thereon. Subsequently, the application liquid for charge transport layer formation is applied onto the charge generating layer and dried to form a charge transport layer thereon. Through the above process, the multi-layer photosensitive member is produced.

The application liquid for charge generating layer formation is prepared through dissolution or dispersion of a charge generating material and a component to be added depending on necessity thereof (for example, a base resin and various additives) in a solvent. The application liquid for charge transport layer formation is prepared through dissolution or dispersion of an electron acceptor compound, a binder resin, a hole transport material, and a component to be added depending on necessity thereof (for example, an additive) in a solvent.

No particular limitations are placed on the respective solvents contained in the application liquid for charge generating layer formation, the application liquid for charge transport layer formation, and the application liquid for single-layer photosensitive layer formation (also referred collectively to below as application liquids), other than that components contained in the respective application liquids should be soluble or dispersible in the corresponding solvents. Examples of the solvents include alcohols (specific examples include methanol, ethanol, isopropanol, and butanol), aliphatic hydrocarbons (specific examples include n-hexane, octane, and cyclohexane), aromatic hydrocarbons (specific examples include benzene, toluene, and xylene), halogenated hydrocarbons (specific examples include dichloromethane, dichloroethane, carbon tetrachloride, and chlorobenzene), ethers (specific examples include dimethyl ether, diethyl ether, tetrahydrofuran, ethylene glycol dimethyl ether, diethylene glycol dimethyl ether, and propylene glycol monomethyl ether), ketones (specific examples include acetone, methyl ethyl ketone, and cyclohexanone), esters (specific examples include ethyl acetate and methyl acetate), dimethyl formaldehyde, dimethyl formamide, and dimethyl sulfoxide. Any one of the solvents listed above may be used or a combination of any two or more of the solvents listed above may be used. A non-halogenated solvent (i.e., a solvent other than a halogenated hydrocarbon) is preferably used as the solvent in order to improve workability in production of the photosensitive member.

Each of the application liquids is prepared by mixing the components in order to disperse the components in the solvent. Examples of an apparatus that can be used for mixing or dispersion include a bead mill, a roll mill, a ball mill, an attritor, a paint shaker, and a ultrasonic disperser.

Each of the application liquids may further contain for example a surfactant in order to improve dispersibility of the components.

No particular limitations are placed on the method by which the application liquid is applied so long as the method enables uniform application of an application liquid onto a conductive substrate. Examples of application methods that can be used include dip coating, spray coating, spin coating, and bar coating.

No particular limitations are placed on the method by which the application liquid is dried other than being a method for evaporating a solvent contained in an application liquid. The drying method may for example be heat treatment (hot-air drying) using a high-temperature dryer or a reduced pressure dryer. The heat treatment is for example performed for at least 3 minutes and no greater than 120 minutes at a temperature of at least 40° C. and no greater than 150° C.

Note that the photosensitive member production method may include either or both of formation of an intermediate layer and formation of a protective layer depending on necessity thereof. Any known methods are appropriately selected each for formation of the intermediate layer and formation of the protective layer.

Examples

The following provides more specific description of the present disclosure through use of Examples. However, the present disclosure is not limited to the scope of the Examples.

<1. Material of Photosensitive Member>

Electron transport materials, a hole transport material, charge generating materials, and a binder resin described below were prepared as materials for forming single-layer photosensitive layers of respective single-layer photosensitive members.

[1-1. Electron Transport Material]

Quinone derivatives (1-1)-(1-7) were each prepared as an electron transport material. The quinone derivatives (1-1)-(1-7) were produced by the following respective methods.

[1-1-1. Production of Quinone Derivative (1-1)]

The quinone derivative (1-1) was produced through reactions represented by respective reaction formulae (r-1) and (r-3) (also referred to below as Reactions (r-1) and (r-3), respectively).

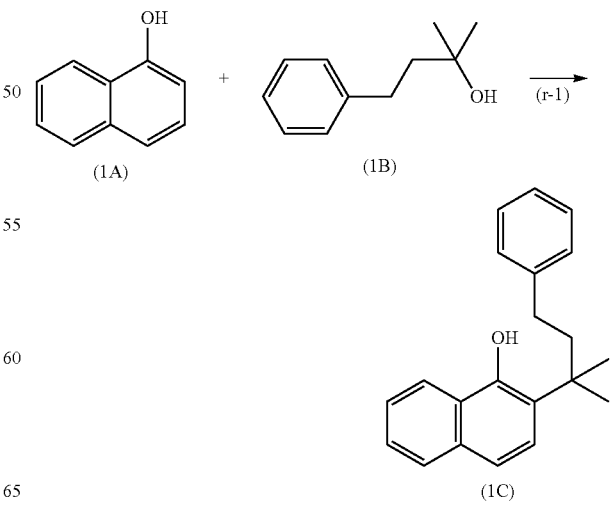

In Reaction (r-1), a naphthol derivative (1A) (1-naphthol) and an alcohol derivative (1B) are caused to react together to yield a naphthol derivative (1C) that is an intermediate product. Specifically, 1.44 g (0.010 moles) of the naphthol derivative (1A), 1.64 g (0.010 moles) of the alcohol derivative (1B), and 0.98 g (0.010 moles) of concentrated sulfuric acid were added into a flask to prepare an acetic acid solution. Then, 0.98 g (0.010 moles) of concentrated sulfuric acid was added dropwise to the flask contents and the flask contents were stirred for eight hours at room temperature. Ion exchanged water and chloroform were added to the flask contents to obtain an organic layer. The organic layer was washed using an aqueous solution of sodium hydroxide for notarization. Subsequently, anhydrous sodium sulfate was added to the organic layer to dry the organic layer. The dried organic layer was subjected to reduced pressure evaporation, thereby yielding a crude product containing the naphthol derivative (1C).

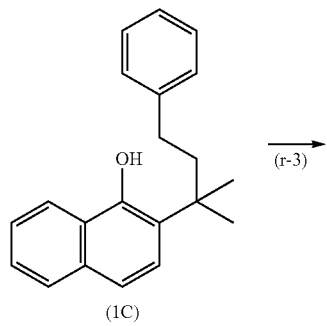

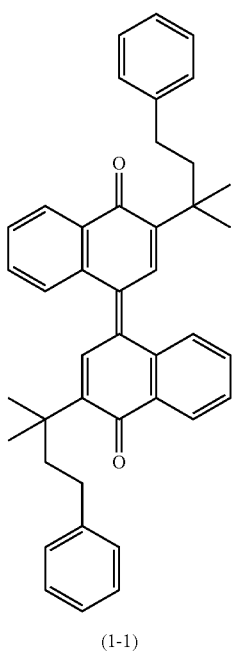

The naphthol derivative (1C) was oxidized in Reaction (r-3) to yield the quinone derivative (1-1). Specifically, the crude product containing the naphthol derivative (1C) and 100 mL of chloroform were added to a flask to prepare a chloroform solution. Then, 2.46 g (0.010 moles) of chloranil was added to the chloroform solution and the flask contents were stirred at room temperature for eight hours. The flask contents were then filtrated, thereby obtaining a filtrate. A solvent of the obtained filtrate was evaporated, thereby yielding a residue. The yielded residue was purified by silica gel column chromatography using chloroform that is a developing solvent. Through the above, the quinone derivative (1-1) was produced. The mass yield of the quinone derivative (1-1) was 1.73 g, and the percentage yield of the quinone derivative (1-1) from the naphthol derivative (1A) was 60 mol %.

[1-1-2. Production of Quinone Derivatives (1-2)-(1-7)]

The quinone derivatives (1-2)-(1-7) were each produced according to the same method as the quinone derivative (1-1) in all aspects other than changes described below. Note that the respective numbers of moles of raw materials added in production of the respective quinone derivatives (1-2)-(1-7) were the same as those added in production of the quinone derivative (1-1).

Table 1 lists respective types of the naphthol derivative (A), the alcohol derivative (B), and the naphthol derivative (C) in Reactions (r-1). Reference sign 1A in a column of Naphthol derivative (A) in Table 1 represents the naphthol derivative (1A). Reference signs 1B-7B in a column of Alcohol derivative (B) represent alcohol derivatives (1B)-(7B), respectively. Reference signs 1C-7C in a column of Naphthol derivative (C) represent naphthol derivatives (1C)-(7C), respectively.

The alcohol derivative (1B) used in Reaction (r-1) was changed to respective alcohol derivatives (2B)-(7B). Through the above, crude products containing the respective naphthol derivatives (2C)-(7C) were yielded through Reaction (r-1) in place of the naphthol derivative (1C).

Table 1 lists respective types of the naphthol derivative (C) and the quinone derivative (1) in Reaction (r-3). Reference signs 1-1-1-7 in a column of Quinone derivative (1) in Table 1 represent the quinone derivatives (1-1)-(1-7), respectively. The crude product containing the naphthol derivative (1C) that was used in Reaction (r-3) was changed to crude products each containing a corresponding one of naphthol derivatives (2C)-(7C). Through the above, respective quinone derivatives (1-2)-(1-7) were produced through Reaction (r-3) in place of the quinone derivative (1-1).

Table 1 lists mass yields and percentage yields of the respective quinone derivatives (1). Note that the alcohol derivatives (2B)-(7B) in Table 1 are represented by the following chemical formulae (2B)-(7B), respectively. Furthermore, the naphthol derivatives (2C)-(7C) are represented by the following chemical formulae (2C)-(7C), respectively.

TABLE 1
| | | | | | | | | |
|---|---|---|---|---|---|---|---|---|
| Reactions (r-1) and (r-3) | | | | | | | | |
| Naphthol derivative (A) | | | Alcohol derivative (B) | | | Quinone derivative (1) | | |
| Type | Additive amount [g] | Additive amount [mole] | Type | Additive amount [g] | Additive amount [mole] | Naphthol derivative (C) | Type | Mass yield [g] | Percentage yield [mol %] |
| 1A | 1.44 | 0.010 | 1B | 1.64 | 0.010 | 1C | 1-1 | 1.73 | 60 |
| 1A | 1.44 | 0.010 | 2B | 1.14 | 0.010 | 2C | 1-2 | 1.55 | 65 |
| 1A | 1.44 | 0.010 | 3B | 1.44 | 0.010 | 3C | 1-3 | 1.61 | 60 |
| 1A | 1.44 | 0.010 | 4B | 1.52 | 0.010 | 4C | 1-4 | 1.52 | 55 |
| 1A | 1.44 | 0.010 | 5B | 2.06 | 0.010 | 5C | 1-5 | 1.98 | 60 |
| 1A | 1.44 | 0.010 | 6B | 2.34 | 0.010 | 6C | 1-6 | 1.97 | 55 |
| 1A | 1.44 | 0.010 | 7B | 1.16 | 0.010 | 7C | 1-7 | 1.56 | 65 |
(2B)
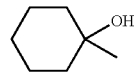
(3B)
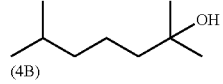
(4B)
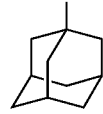
(5B)
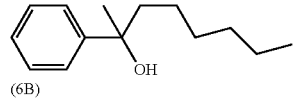
(6B)
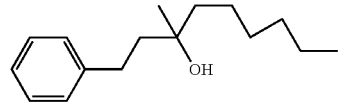
(7B)
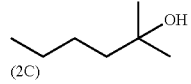
(2C)
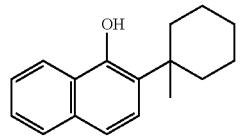 [SMILES: CC1(c2ccc3ccccc3c2O)CCCCC1]
(3C)
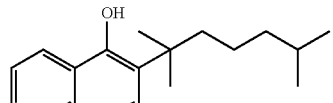
(4C)
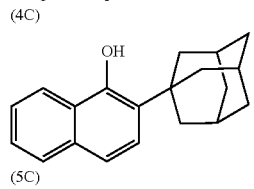
(5C)
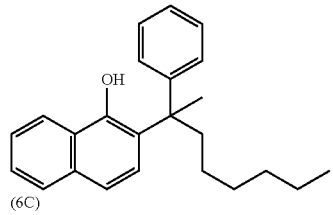
(6C)

TABLE 1-continued

| | Reactions (r-1) and (r-3) | | | | | | | |
|---|---|---|---|---|---|---|---|---|
| Naphthol derivative (A) | | Alcohol derivative (B) | | | | Quinone derivative (1) | | |
| Type | Additive amount [g] | Additive amount [mole] | Type | Additive amount [g] | Additive amount [mole] | Naphthol derivative (C) | Type | Mass yield [g] | Percentage yield [mol %] |

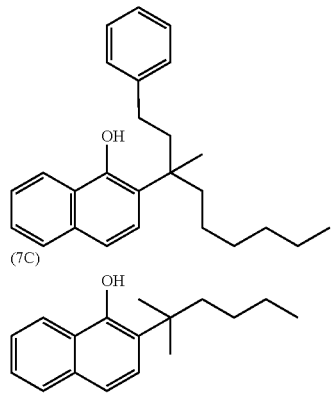

(7C)

Figure 3:
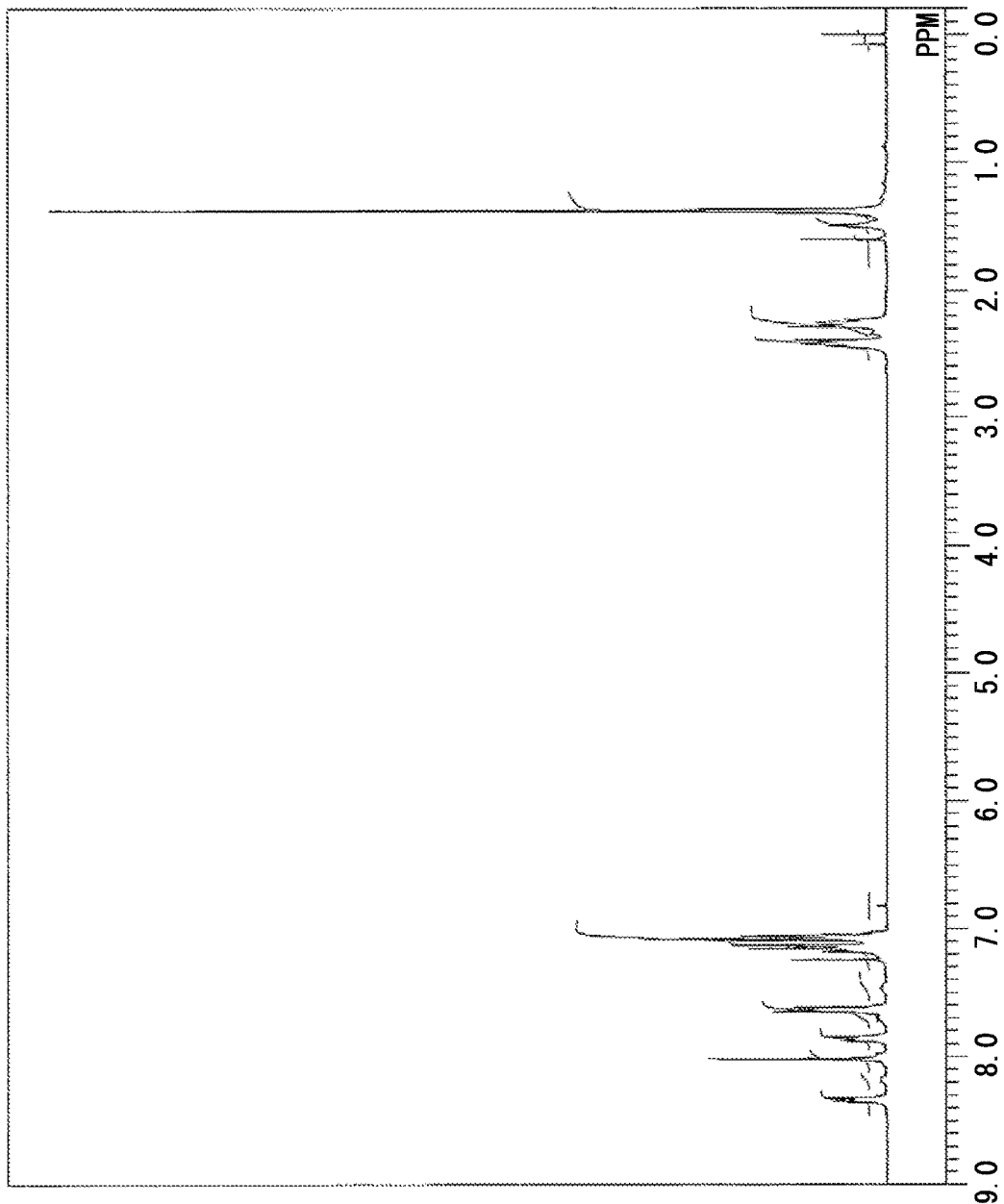
FIG. 3 is a $^1$H-NMR spectrum of a quinone derivative (1-1).
Figure 4:
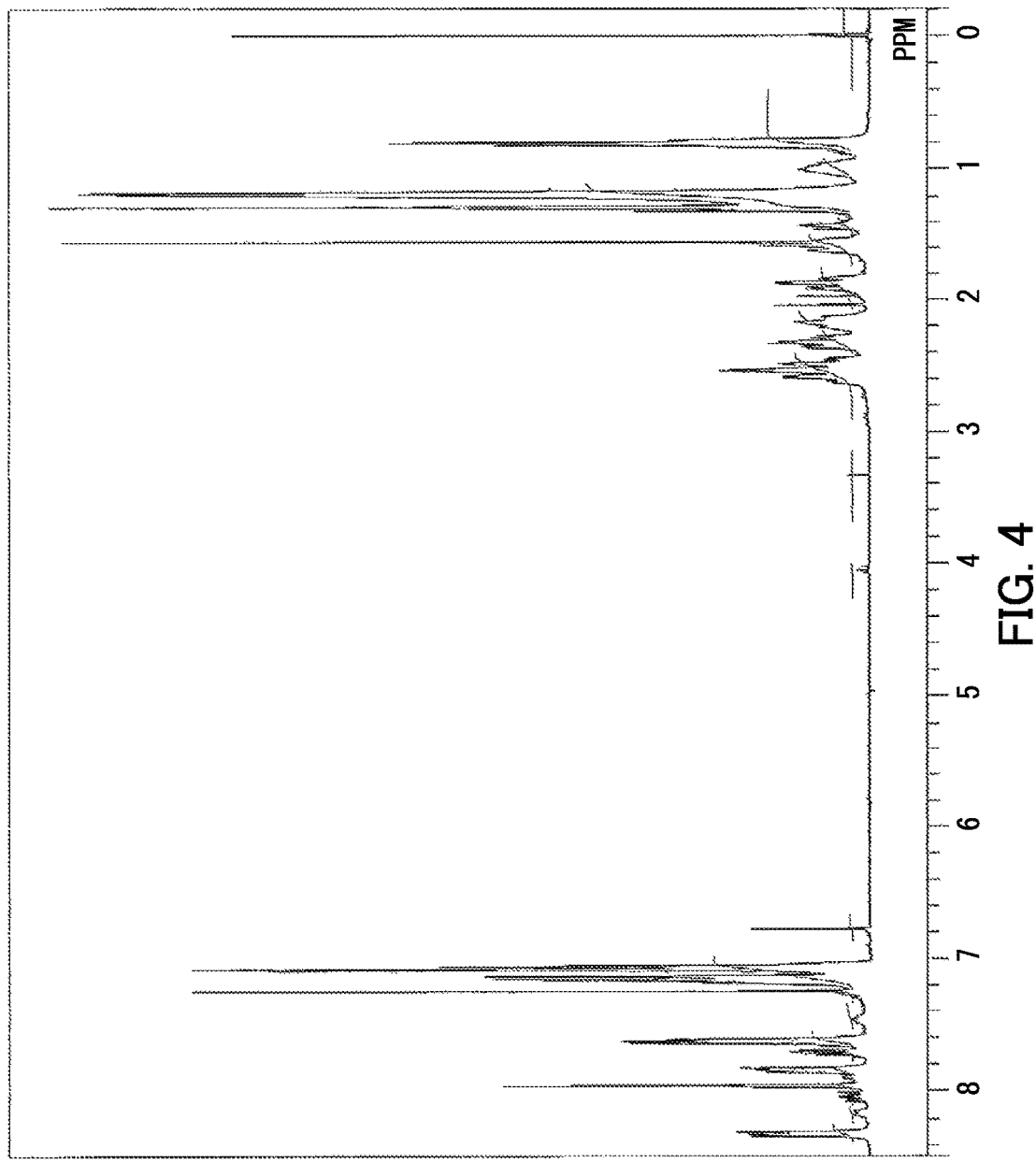
FIG. 4 is a $^1$H-NMR spectrum of a quinone derivative (1-6).

Subsequently, $^1$H-NMR spectra of the respective produced quinone derivatives (1-1)-(1-7) were measured using a proton nuclear magnetic resonance spectrometer (product of JASCO Corporation, 300 MHz). $CDCl_3$ was used as a solvent. Tetramethylsilane (TMS) was used as an internal standard sample. The quinone derivatives (1-1) and (1-6) among the quinone derivatives (1-1)-(1-7) are referred to as representative examples. FIGS. 3 and 4 indicate $^1$H-NMR spectra of the quinone derivatives (1-1) and (1-6), respectively. In each of FIGS. 3 and 4, a vertical axis indicates signal strength (unit: optional unit) while the horizontal axis indicates chemical shift (unit: ppm). Values of chemical shifts of the respective quinone derivatives (1-1) and (1-6) are indicated below.

Quinone derivative (1-1): $^1$H-NMR (300 MHz, $CDCl_3$), δ=8.32-8.35 (m, 2H), 8.02 (s, 2H), 7.84-7.88 (m, 2H), 7.60-7.67 (m, 4H), 7.03-7.18 (m, 10H), 2.39-2.45 (m, 4H), 2.22-2.29 (m, 4H), 1.38 (s, 12H).

Quinone derivative (1-6): $^1$H-NMR (300 MHz, $CDCl_3$), δ=8.31-8.35 (m, 2H), 7.97 (s, 2H), 7.83-7.87 (m, 2H), 7.62-7.73 (m, 4H), 7.03-7.25 (m, 10H), 2.48-2.60 (m, 4H), 2.17-2.37 (m, 4H), 1.86-1.98 (m, 2H), 1.56-1.63 (m, 2H), 1.19-1.33 (m, 22H), 0.81 (t, 6H).

The $^1$H-NMR spectra and the chemical shifts were used to confirm that the quinone derivatives (1-1) and (1-6) had been obtained. As to the other quinone derivatives (1-2)-(1-5) and (1-7), the $^1$H-NMR spectra and the chemical shifts were used likewise to confirm that the quinone derivatives (1-2)-(1-5) and (1-7) had been obtained.

[1-1-3. Preparation of Compounds (E-1) and (E-2)]

Compounds represented by respective chemical formulae (E-1) and (E-2) (also referred to below as compounds (E-1) and (E-2), respectively) were each prepared as an electron transport material.

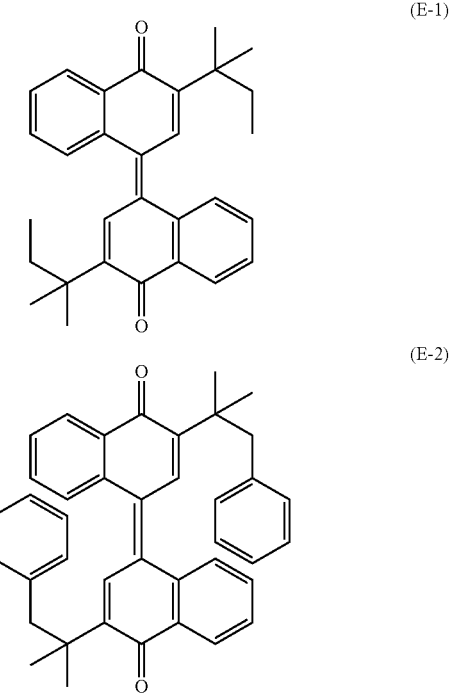

[1-2. Hole Transport Material]

The compound (H-1) described in the second embodiment was prepared as a hole transport material.

[1-3. Charge Generating Material]

The compounds (C-1) and (C-2) described in the second embodiment were each used as a charge generating material. The compound (C-1) was a metal-free phthalocyanine (X-form metal-free phthalocyanine) represented by chemical formula (C-1). The compound (C-1) has a crystal structure of X-form.

The compound (C-2) was a titanyl phthalocyanine (Y-form titanyl phthalocyanine) represented by chemical formula (C-2). The compound (C-2) has a crystal structure of Y-form.

[1-4. Binder Resin]

A Z-type polycarbonate resin (Resin-1) ("Panlite" (registered Japanese trademark) TS-2050" produced by Teijin Limited, viscosity average molecular weight: 50,000) was prepared as a binder resin.

<2. Single-Layer Photosensitive Member Production>

Single-layer photosensitive members (A-1)-(A-14) and (B-1)-(B-4) were produced using materials for photosensitive layer formation.

[2-1. Production of Single-Layer Photosensitive Member (A-1)]

To a container, 2 parts by mass of the compound (C-1) that is a charge generating material, 50 parts by mass of the compound (H-1) that is a hole transport material, 30 parts by mass of the quinone derivative (1-1) that is an electron transport material, 100 parts by mass of a Z-type polycarbonate resin (Resin-1) that is a binder resin, and 600 parts by mass of tetrahydrofuran that is a solvent were added. The container contents were mixed for 12 hours using a ball mill in order to disperse the materials in the solvent. Through the above process, an application liquid for single-layer photosensitive layer formation was prepared. The application liquid for single-layer photosensitive layer formation was applied onto a drum-shaped aluminum support member that is a conductive substrate by dip coating. The applied application liquid for single-layer photosensitive layer formation was hot-air dried for 80 minutes at a temperature of 120° C. Through the above process, a single-layer photosensitive layer (film thickness: 30 μm) was formed on the conductive substrate. The single-layer photosensitive member (A-1) was obtained as a result of the process described above.

[2-2. Production of Single-Layer Photosensitive Members (A-2)-(A-14) and (B-1)-(B-4)]

The single-layer photosensitive members (A-2)-(A-14) and (B-1)-(B-4) were produced according to the same method as the single-layer photosensitive member (A-1) in all aspects other than changes described below. The compound (C-1) used as a charge generating material in production of the single-layer photosensitive member (A-1) was changed to respective charge generating materials listed in Table 2. The quinone derivative (1-1) used as an electron transport material in production of the single-layer photosensitive member (A-1) was changed to respective electron transport materials listed in Table 2. Note that Table 2 indicates respective constituents of the photosensitive members (A-1)-(A-14) and (B-1)-(B-4). In Table 2, CGM, HTM, and ETM represent a charge generating material, a hole transport material, and an electron transport material, respectively. In Table 2, x-$H_2$Pc and Y-TiOPc in a column of CGM represent X-form metal-free phthalocyanine (the compound C-1) and Y-form titanyl phthalocyanine (the compound C-2), respectively. The compound (H-1) is represented by H-1 in a column of HTM. The quinone derivatives (1-1)-(1-7) and compounds (E-1) and (E-2) are represented by 1-1-1-7 and E-1 and E-2 in a column of ETM, respectively.

<3 Evaluation of Photosensitive Members>

[3-1. Evaluation of Single-Layer Photosensitive Member Electrical Properties (Sensitivity Characteristics)]

Electrical properties (sensitivity characteristics) of the produced single-layer photosensitive members (A-1)-(A-14) and (B-1)-(B-4) were evaluated. The electrical properties were evaluated in an environment at a temperature of 23° C. and a relative humidity of 50% RH.

The surface of each of the single-layer photosensitive members was positively charged using a drum sensitivity test device (product of Gen-Tech, Inc.). The rotational speed of the single-layer photosensitive member was set at 31 rpm as a charge condition. The surface potential of the single-layer photosensitive member directly after charging was set at +600 V. Next, monochromatic light (wavelength: 780 nm, half-width: 20 nm, light energy: 1.5 μJ/cm$^2$) was extracted from white light of a halogen lamp using a bandpass filter. The surface of the single-layer photosensitive member was irradiated with the extracted monochromatic light. The surface potential of the single-layer photosensitive member when 0.5 seconds elapsed from irradiation was measured. The measured surface potential was taken to be a post-exposure potential ($V_L$, unit: V). The measured sensitivity potentials ($V_L$) of the respective single-layer photosensitive members are listed in Table 2. The smaller the absolute value of the post-exposure potential ($V_L$) is, the more excellent the sensitivity characteristics of a single-layer photosensitive member are.

[3-2. Evaluation of Single-Layer Photosensitive Member Crack Resistance]

Crack resistance of the produced single-layer photosensitive members (A-1)-(A-14) and (B-1)-(B-4) were evaluated. Crack resistance was evaluated in an environment at a temperature of 23° C. and a relative humidity of 50% RH.

After oil (oleic triglyceride) was applied to ten areas in the surface of each of the single-layer photosensitive members, the multi-layer electrophotographic photosensitive member was left to stand for five days. Thereafter, the surface of the photosensitive member to which the oil had been applied was observed using an optical microscope ("MM11" produced by NIKON CORPORATION, magnification: 100×) to check the presence or absence of a crack. The number of areas among the oil-applied areas in which a crack was observed was counted. Crack resistance was evaluated based on the counted number of portions in which a crack was observed based on the following references. Note that evaluation results A, B, and C each were determined to be an evaluation pass.

Evaluation result A (very good): No portion in which a crack was observed was present.

Evaluation result B (good): One to two portions in which a crack was observed were present.

Evaluation result C (mediocre): Three to four portions in which a crack was observed were present.

Evaluation result D (bad): Five or more portions in which a crack was observed were present.

TABLE 2

| | Photosensitive member | Photosensitive layer | | | Electrical properties Post-exposure potential $V_L$ (V) | Crack resistance |
|---|---|---|---|---|---|---|
| | | CGM | HTM | ETM | | |
| Example 1 | A-1 | x-H$_2$Pc | H-1 | 1-1 | +118 | A |
| Example 2 | A-2 | Y-TiOPc | H-1 | 1-1 | +114 | A |
| Example 3 | A-3 | x-H$_2$Pc | H-1 | 1-2 | +120 | B |
| Example 4 | A-4 | Y-TiOPc | H-1 | 1-2 | +116 | B |
| Example 5 | A-5 | x-H$_2$Pc | H-1 | 1-3 | +121 | A |
| Example 6 | A-6 | Y-TiOPc | H-1 | 1-3 | +116 | A |
| Example 7 | A-7 | x-H$_2$Pc | H-1 | 1-4 | +122 | B |
| Example 8 | A-8 | Y-TiOPc | H-1 | 1-4 | +118 | B |
| Example 9 | A-9 | x-H$_2$Pc | H-1 | 1-5 | +125 | B |
| Example 10 | A-10 | Y-TiOPc | H-1 | 1-5 | +120 | B |
| Example 11 | A-11 | x-H$_2$Pc | H-1 | 1-6 | +119 | A |
| Example 12 | A-12 | Y-TiOPc | H-1 | 1-6 | +115 | A |
| Example 13 | A-13 | x-H$_2$Pc | H-1 | 1-7 | +120 | B |
| Example 14 | A-14 | Y-TiOPc | H-1 | 1-7 | +116 | C |
| Comparative Example 1 | B-1 | x-H$_2$Pc | H-1 | E-1 | +124 | D |
| Comparative Example 2 | B-2 | Y-TiOPc | H-1 | E-1 | +119 | D |
| Comparative Example 3 | B-3 | x-H$_2$Pc | H-1 | E-2 | +121 | D |
| Comparative Example 4 | B-4 | Y-TiOPc | H-1 | E-2 | +115 | D |

As indicated in Table 2, the photosensitive layers of the respective photosensitive members (A-1)-(A-14) each contain a corresponding one of the charge generating materials, the hole transport material, and corresponding one of the quinone derivatives (1-1)-(1-7) that each are an electron transport material. The quinone derivatives (1-1)-(1-7) each are a quinone derivative represented by general formula (1). The photosensitive members (A-1)-(A-14) are graded any of A, B, and C in evaluation of crack resistance.

As indicated in Table 2, the photosensitive layers of the respective photosensitive members (B-1)-(B-4) each contain a corresponding one of the charge generating materials, the hole transport material, and either one of the compounds (E-1) and (E-2) that each are an electron transport material. The compounds (E-1) and (E-2) each are not the quinone derivative (1). The photosensitive members (B-1)-(B-4) are graded D in evaluation of crack resistance.

It is clear that crack resistance of a photosensitive member is improved by using a quinone derivative represented by general formula (1) when compared with the use of the compound (E-1) or (E-2). It is also clear that the photosensitive members (A-1)-(A-14) are more excellent in crack resistance than the photosensitive members (B-1)-(B-4).

As indicated in Table 2, the photosensitive layers of the respective photosensitive members (A-1), (A-2), (A-5), (A-6), (A-11), and (A-12) each contain any one of the quinone derivatives (1-1), (1-3), and (1-6) that each are an electron transport material. One or two of $R^1$, $R^2$, and $R^3$ in the quinone derivatives (1-1), (1-3), and (1-6) each represent an alkyl group having 1 to 3 carbon atoms that has a phenyl group or an alkyl group having 5 to 7 carbon atoms. All other of $R^1$, $R^2$, and $R^3$ represents a methyl group. At least two of $R^1$, $R^2$, and $R^3$ are not bonded together to form a ring. One or two of $R^4$, $R^5$, and $R^6$ represent an alkyl group having 1 to 3 carbon atoms that has a phenyl group or an alkyl group having 5 to 7 carbon atoms. All other of $R^4$, $R^5$, and $R^6$ represents a methyl group. At least two of $R^4$, $R^5$, and $R^6$ are not bonded together to form a ring. The photosensitive members (A-1), (A-2), (A-5), (A-6), (A-11), and (A-12) are graded A in evaluation of crack resistance.

As indicated in Table 2, the photosensitive layers of the respective photosensitive members (A-3), (A-4), (A-7)-(A-10), (A-13), and (A-14) each contain any one of the quinone derivatives (1-2), (1-4), (1-5), and (1-7) that each are an electron transport material. At least two of $R^1$, $R^2$, and $R^3$ are bonded together to form a ring and at least two of $R^4$, $R^5$, and $R^6$ are bonded together to form a ring in the respective quinone derivatives (1-2) and (1-4). At least one of $R^1$, $R^2$, and $R^3$ represents a phenyl group and at least one of $R^4$, $R^5$, and $R^6$ represents a phenyl group in the quinone derivative (1-5). At least one of $R^1$, $R^2$, and $R^3$ represents an n-butyl group and at least one of $R^4$, $R^5$, and $R^6$ represents an n-butyl group in the quinone derivative (1-7). The photosensitive members (A-3), (A-4), (A-7)-(A-10), (A-13), and (A-14) are graded B in evaluation of crack resistance.

It is clear that the use of the quinone derivatives (1-1), (1-3), or (1-6) can improve crack resistance of the photosensitive member more than the use of the quinone derivatives (1-2), (1-4), (1-5), and (1-7). It is also clear that the photosensitive members (A-1), (A-2), (A-5), (A-6), (A-11), and (A-12) are more excellent in crack resistance than the photosensitive members (A-3), (A-4), (A-7)-(A-10), (A-13), and (A-14).

What is claimed is:
1. A quinone derivative that is represented by any one of chemical formulae (1-1), (1-3), and (1-6)

(1-1)

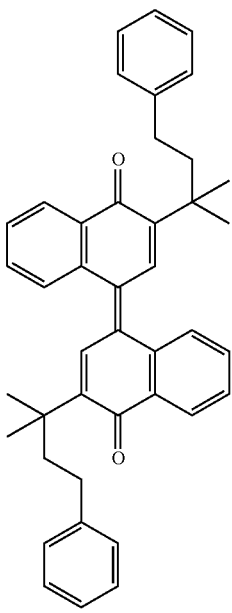

(1-3)

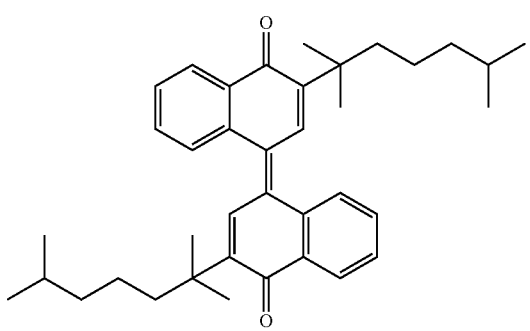

(1-6)

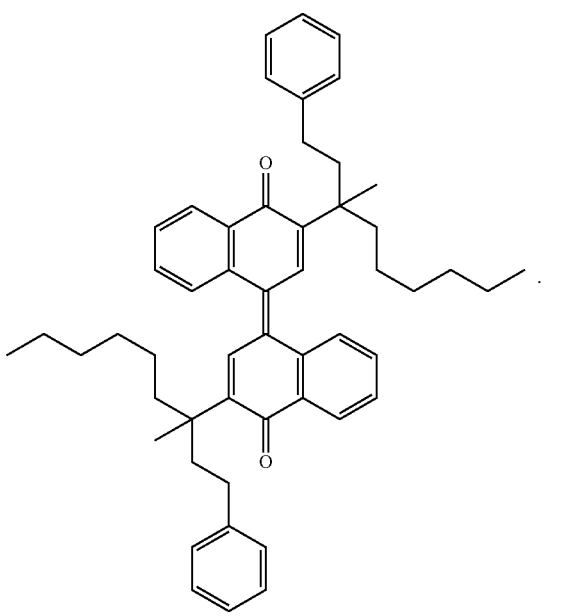

2. An electrophotographic photosensitive member comprising a conductive substrate and a photosensitive layer, wherein
the photosensitive layer contains a charge generating material, a hole transport material, a binder resin, and the quinone derivative according to claim 1.

3. The electrophotographic photosensitive member according to claim 2, wherein
the charge generating material contains an X-form metal-free phthalocyanine or a Y-form titanyl phthalocyanine.

4. The electrophotographic photosensitive member according to claim 2, wherein
the hole transport material contains a compound represented by general formula (2) shown below:

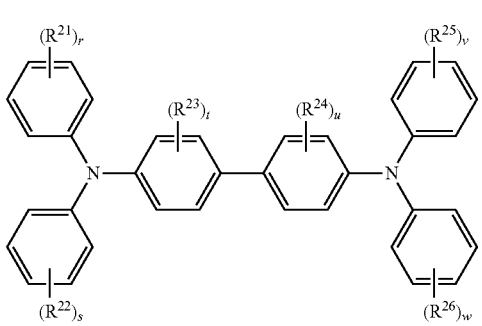

where, in the general formula (2),
$R^{21}$, $R^{22}$, $R^{23}$, $R^{24}$, $R^{25}$, and $R^{26}$ each represent, independently of one another, an alkyl group having 1 to 6 carbon atoms or an alkoxy group having 1 to 6 carbon atoms,
r, s, v, and w each represent, independently of one another, an integer of at least 0 and no greater than 5, and
t and u each represent, independently of one another, an integer of at least 0 and no greater than 4.

5. The electrophotographic photosensitive member according to claim 2, wherein
the photosensitive layer is a single-layer photosensitive layer.

* * * * *